United States Patent [19]

Harandi et al.

[11] Patent Number: 5,095,159
[45] Date of Patent: Mar. 10, 1992

[54] ETHER AND HYDROCARBON PRODUCTION

[75] Inventors: Mohsen N. Harandi, Lawrenceville; Hartley Owen, Belle Mead, both of N.J.

[73] Assignee: Mobil Oil Corporation, Fairfax, Va.

[21] Appl. No.: 616,530

[22] Filed: Nov. 21, 1990

[51] Int. Cl.$^5$ ............................................... C07C 5/48
[52] U.S. Cl. .................................... 585/408; 585/418
[58] Field of Search ............... 585/407, 408, 639, 640, 585/418

[56] References Cited

U.S. PATENT DOCUMENTS

| | | | |
|---|---|---|---|
| 4,544,781 | 10/1985 | Chao et al. | 585/408 |
| 4,814,536 | 3/1989 | Yurchak | 585/640 |
| 4,835,329 | 5/1989 | Harandi | 585/415 |
| 4,854,939 | 8/1989 | Harandi et al. | 585/415 |
| 4,857,667 | 8/1989 | Harandi et al. | 585/408 |
| 4,886,925 | 12/1989 | Harandi | 585/314 |
| 4,891,463 | 1/1990 | Chu | 585/418 |
| 5,001,292 | 3/1991 | Harandi et al. | 585/408 |

Primary Examiner—Anthony McFarlane
Attorney, Agent, or Firm—Alexander J. McKillop; Charles J. Speciale; L. G. Wise

[57] ABSTRACT

An integrated process is disclosed that substantially reduces the cost of producing MTBE and other alkyl tertalkyl ethers by eliminating a major portion of the equipment and operating costs associated with the downstream processing of the etherification reactor effluent. The integrated process combines the process for the etherification of iso-olefins and methanol, or other alkanols, to produce methyl tertiary alkyl ethers such as MTBE and/or TAME with the catalytic process for converting feedstock such as oxygenates, light olefins and paraffins to higher molecular weight hydrocarbons. Unconverted reactants from the etherification reaction, which may comprise unreacted alkanol and unreacted hydrocarbons or just unreacted hydrocarbons, are separated from the product ethers and passed to the catalytic conversion process reactor for conversion to gasoline boiling range hydrocarbons.

16 Claims, 1 Drawing Sheet

ETHER AND HYDROCARBON PRODUCTION

This application is a division of U.S. patent application Ser. No. 07/422,203, filed Oct. 16, 1989, now U.S. Pat. No. 5,001,292; which is a continuation-in-part of abandoned application Ser. No. 07/349,555, filed May 9, 1989, which is a division of Ser. No. 07/130,260, filed Dec. 8, 1987, now U.S. Pat. No. 4,854,939, incorporated herein by reference.

BACKGROUND OF THE INVENTION this invention relates to methods for reacting aliphatic alcohol (alkanol), such as methanol or the like and olefinic hydrocarbons to produce lower alkyl tertiary-alkyl ethers without the need for recycling unreacted alkanol and/or hydrocarbon. In particular, this invention relates to a continuous integrated system for converting methanol to high octane ether and gasoline by etherifying hydrocarbons containing iso-olefins, such as the $C_3$-$C_4$ olefinic cracked gas streams obtained from fluid catalytic cracking (FCC) products.

It is known that isobutylene and other isoalkenes produced by hydrocarbon cracking may be reacted with methanol and other C1-C4 lower aliphatic alcohols over an acidic catalyst to provide methyl tertiary butyl ether (MTBE) or the like. Generally, it is known that asymmetrical ethers having the formula $(CH_3)_3C$—O—R, where R is a C1-C4 alkyl radical, are particularly useful as octane improvers for liquid fuels, especially gasoline.

MTBE, ethyl t-butyl ether (ETBE), tert-amyl methyl ether (TAME) and isopropyl t-butyl ether (IPTBE) are known to be high octane ethers. The article by J. D. Chase, et al., *Oil and Gas Journal*, Apr. 9, 1979, discussed the advantages one can achieve by using such materials to enhance gasoline octane. The octane blending number of MTBE when 10% is added to a base fuel (R+(=91) is about 120. For a fuel with a low motor rating (M+O=83) octane, the blending value of MTBE at the 10% level is about 103. On the other hand, for an (R+O) of 95 octane fuel, the blending value of 10% MTBE is about 114.

While its is known that isobutylene and/or isoamylene may be reacted with methanol over an acidic catalyst to provide MTBE and/or TAME, a problem of major importance in these processes is the separation of unreacted methanol and hydrocarbons from the etherification reaction product due to the proclivity of methanol to form a very dilute azeotropic mixture with hydrocarbons and the strong solubility of methanol in both water and hydrocarbons. But, to achieve high iso-olefin conversion to ethers equimolar or larger quantities of methanol are preferred in the etherification reaction, producing unreacted methanol. Due largely to these factors, the cost associated with methanol separation and recycling in the etherification reaction represents a large part of the cost of the total etherification process.

In recent years, a major development within the petroleum industry has been the discovery of the special catalytic capabilities of a family of zeolite catalyst based upon medium pore size shape selective metallosilicates. Discoveries have been made leading to a series of analogous processes drawn from the catalytic capability of zeolites. Depending upon various conditions of space velocity, temperature and pressure lower oxygenates, such as methanol can be converted in the presence of zeolite type catalyst to olefins which can oligomerize to provide gasoline or distillate or can be converted further to produce aromatics. Recognizing the commonality of the feedstock and product between etherification reactions to produce high octane gasoline and zeolite catalyzed conversion reactions, interest has focused on the applicability of combined processes as an approach to advance the art in the production of high octane gasoline.

It has been discovered that under certain conditions substantial improvements in the art of alkyl tert-alkyl ether production can be realized in a combination or integration of etherification and hydrocarbon conversion process based upon zeolite type catalysis. Accordingly, it is an object of this invention to provide a novel integrated process for the production alkyl tert-alkyl ethers, particularly MTBE and/or TAME.

Another object of this invention is to provide a novel and cost effective process for the production of high octane alkyl tertiary alkyl ethers without recycling unreacted alkanol and/or unreacted hydrocarbons to the etherification reactor.

Yet another object of the present invention is to provide a novel process of the production of high octane gasoline rich in aromatics utilizing unreacted methanol from etherification.

SUMMARY OF THE INVENTION

An integrated process has been discovered that substantially reduces the cost of producing ether by eliminating a major portion of the equipment and operating costs associated with the downstream processing of the etherification reactor effluent. The integrated process combines the process for the etherification of iso-olefins and methanol, or other alkanols, to produce methyl tertiary alkyl ethers such as MTBE and/or TAME with the catalytic process for converting feedstock such as oxygenates, light olefins and paraffins to higher molecular weight hydrocarbons. Unconverted reactants from the etherification reaction, which may comprise unreacted alkanol and/or unreacted hydrocarbons, are separated form the product ethers and passed to the catalytic reactor for conversion to gasoline boiling range hydrocarbons.

More particularly, a continuous process for converting alkanol to alkyl tertiary-alkyl ethers and gasoline boiling range hydrocarbons has been discovered which comprises the steps of:

(a) contacting alkanol and a light olefinic hydrocarbon stream rich in isobutylene and other $C_4$ isomeric hydrocarbons under iso-olefins etherification conditions in an etherification reaction zone containing acid etherification catalyst;

(b) separating the etherification effluent form step (a) to recover an upper stream comprising unreacted alkanol and light olefinic hydrocarbon and a liquid stream containing alkyl tertiary-butyl ether; and (c) contacting said unreacted alkanol and light hydrocarbon stream with acidic catalyst, preferably medium pore metallosilicate catalyst, under alkanol and hydrocarbon conversion conditions whereby gasoline boiling range hydrocarbons are produced.

DETAILED DESCRIPTION OF THE INVENTION

Figure 1:
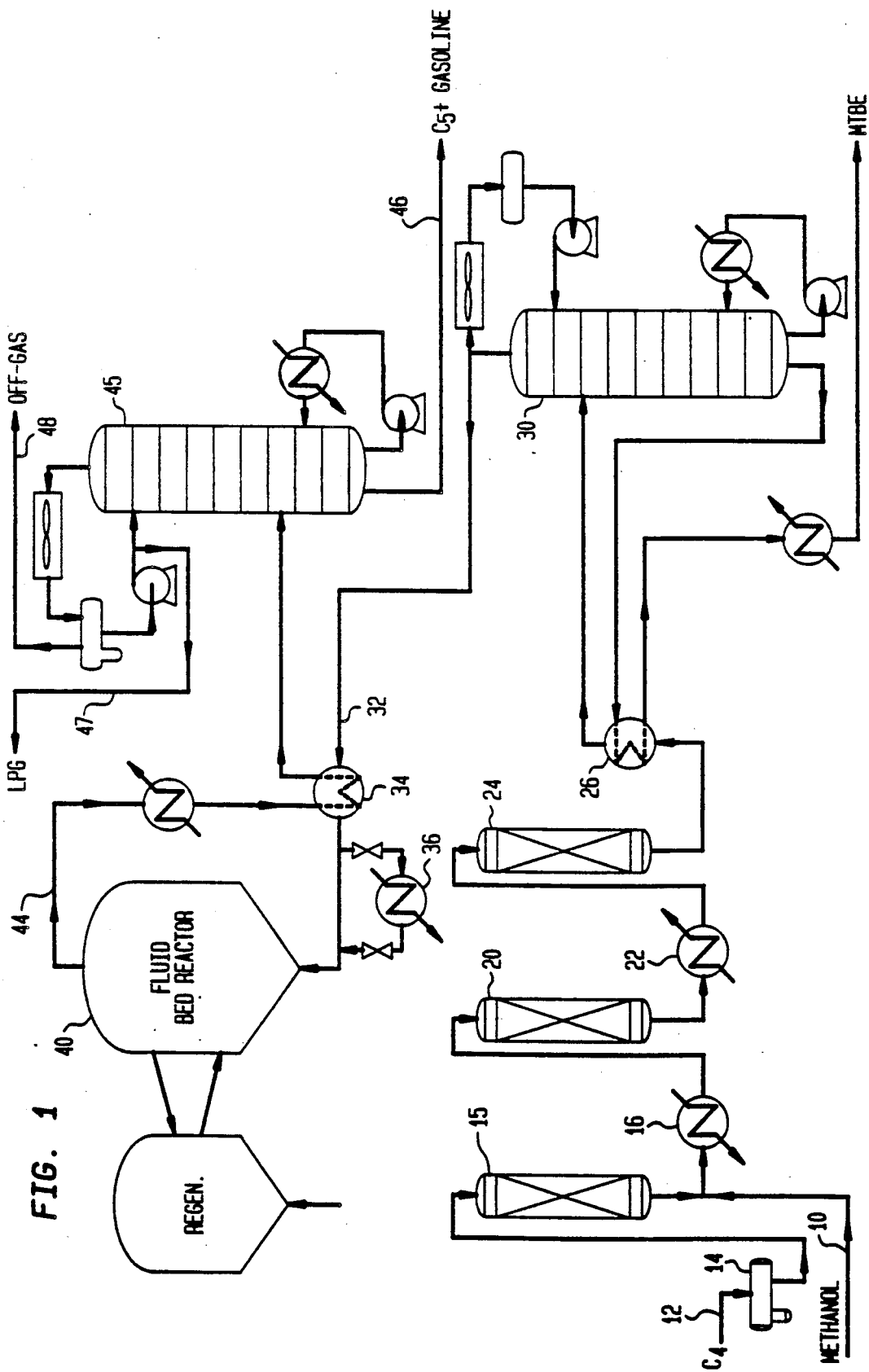
FIG. 1 of the drawing is a schematic etherification process flowsheet depicting the present invention.

Typical feedstock materials for etherification reactions include olefinic streams, such as FCC light cracked gas containing butene isomers, often in mixture with substantial amounts of propene, propane, n-butane and isobutane. The $C_4$ components usually contain a major amount of unsaturated compounds, such as 10-25% isobutylene, 25-55% linear butenes, and small amounts of butadiene. Also, $C_4+$ heavier olefinic hydrocarbon streams may be used, particularly mixtures of isobutylene and isoamylene. These aliphatic streams are produced in a variety of petroleum refinery operation such as catalytic cracking of gas oil or the like. The dry methanol feedstream should preferably have a purity of about 99.8 wt. %.

Suitable alkanols include $C_1$-$C_4$ primary or secondary alcohols, including methanol, ethanol, 1-propanol, isopropanol, 1-butanol, 2-butanol and mixtures thereof.

Referring to FIG. 1 of the drawing, a continuous stream of $C_4$-olefinic hydrocarbon liquid is introduced via conduit 12 to pre-separation unit 14 and guard bed 15 and mixed with dry methanol (MeOH) feedstock introduced via conduit 10. The combined streams are pressurized to about 1190 kPa (170 psig), heated in exchanger 16 to a temperature of about 55° C. (130° F.) and passed to a first serial reactor 20 for conversion of methanol in contact with acid etherification catalyst, preferably solid polysulfonic acid resin such as sulfonated vinyl aromatic resins. Amberlyst 15 from Rohm and Haas is a preferred catalyst. From first reactor 20 the reaction stream is cooled in exchanger 22 from about 70° C. to 55° C. and further reacted in a second serial reactor 24, where the reaction is carried partially to completion (e.g., 96% conversion of isobutylene).

the reactor effluent stream containing MTBE, methanol and unreacted light hydrocarbons is preheated in exchanger 26 and fed to debutanizer fractionation tower 30. In separation unit 30 the $C_5+$ methyl tert-alkyl ether product is recovered as a liquid product, along with byproduct dimer or other heavier hydrocarbons in the effluent. Tower overhead vapor comprising unreacted $C_4$—light hydrocarbons and methanol are passed via conduit 32 and heat exchange means 34, 36 to an effluent upgrading reactor 40. The catalytic conversion unit 40 is preferably a fluid bed unit, equipped with a catalyst regenerator 42. Reactor effluent may be fractionated in a debutanizer tower 45 to recover a gasoline product stream 46, $C_3$-$C_4$ LPG stream 47, and off-gas 48.

The methanol-containing stream, preferably a vapor stream, may be coreacted with olefinic light gas and/or other reactive hydrocarbon feedstreams in an oligomerization/aromatization reaction section, as described by Avidan et al. in U.S. Pat. Nos. 4,547,616 and 4,746,762 and by Owen et al. in U.S. Pat. No. 4,827,046 and U. S. Pat. No. 4,831,203, incorporated herein by reference. Optionally, FCC light gas containing ethene or propene may be injected at the bottom of the fluidized bed reaction zone and converted along with the unreacted methanol containing fractions of the light hydrocarbon etherification effluent stream.

The following Example provides a detailed illustration of the process of this invention for a refinery operation processing methanol and $C_4$ feedstock to produce MTBE and hydrocarbon conversion products containing about 22 mole percent of gasoline products. The gasoline products are about 55 weight percent aromatics, 15 weight percent olefins, with the balance paraffins.

EXAMPLE

About 530.36 moles/hr of feedstock is passed to the etherification reactor system as described in FIG. 1. The feedstock contains 69 moles/hr of methanol and hydrocarbons consisting of 12 moles/hr of $C_3$'s, 129.45 moles/hr of isobutane, 219.18 moles/hr of 1-butene, 25.09 moles/hr of n-butane and 71.18 moles/hr of isobutene and 4.46 moles/hr of $C_5+$ hydrocarbons. Following etherification, the effluent therefrom contains 66.87 moles/hr of MTBE, 2.09 moles/hr of unreacted methanol, 2.47 moles/hr of unreacted isobutene, 12 moles/hr of $C_3$'s, 129.45 moles/hr of isobutane, 219.18 moles/hr of 1-butene, 25.09 moles/hr of n-butane and 4.46 moles/hr of $C_5+$. MTBE is recovered following debutanization and debutanized overhead vapor is passed to the fluidized bed zeolite conversion zone for contact with ZSM-5 catalyst under conversion conditions previously described in reference to FIG. 1. The conversion is carried out at a temperature of 480° C. (900° F.) and 925 kPa (135 psia) to produce 354.16 moles/hr of effluent. The product stream consists essentially of water (2.09 moles/hr), $C_5+$ gasoline (77.87 moles/hr), isobutene (6.63 moles/hr), n-butane (39.21 moles/hr), 1-butene (6.63 moles/hr), isobutane (153.72 moles/hr), propane (37.98 moles/hr), propene (14.32 moles/hr), ethane (3.84 moles/hr), ethene (8.68 moles/hr), and methane (3.20 moles/hr).

Etherification Operation the reaction of methanol with isobutylene and isoamylenes at moderate conditions with a resin catalyst is known technology, as provided by R. W. Reynolds, et al., *The Oil and Gas Journal*, June 16, 1975, and S. Pecci and T. Floris, *Hydrocarbon Processing*, December 1977. An article entitled "MTBE and TAME—A Good Octane Boosting Combo, " by J. D. Chase, et al., *The Oil and Gas Journal*, Apr. 9, 1979, pages 149–152, discusses the technology. A preferred catalyst is a polymeric sulfonic acid exchange resin such as Amberlyst 15.

In the etherification process it is known that alkanol and iso-olefins may be reacted in equimolar quantities of either reactant may be in molar excess to influence the complete conversion of the other reactant. Because etherification is an incomplete reaction the etherification effluent comprises unreacted alkanol and unreacted hydrocarbons. On a stoichiometric equivalencies basis, equimolar quantities of methanol and iso-olefins are advantageous but an excess between 2 and 200% of either component can be passed to the etherification reaction unit. In the present invention, the molar ratio of alkanol to iso-olefin, such as methanol to iso-butylene, can be between 0.7 and 2, but preferably the molar ratio is 1 for methanol to isobutylene. Advantageously, the excess methanol may be about 40% or more when the hydrocarbon feedstream comprises significant quantity of isoamylenes, but equimolar quantities are preferred when the hydrocarbon feedstream consists essentially of $C_4$ hydrocarbons.

Iso-olefins or isoalkenes in this invention are those having the formula $R_2C=CH_2$ or $R_2C=CHR$. Alkanols which may be used in the present invention include methanol, ethanol, 1-propanol, isopropanol, 1-butanol and 2-butanol. In this invention oxygenate or lower oxygenates refers to $C_1$-$C_5$ alcohols, ethers, aldehydes, esters and the like.

METHANOL AND/OR HYDROCARBONS CONVERSION

It is advantageous to convert substantially the entire stream of unreacted alcohol and light olefinic components recovered form etherification effluent by acid zeolite catalysis, thus providing a once-through process without expensive alcohol recycle to the etherification unit. Zeolite conversion technology for upgrading lower aliphatic hydrocarbons and oxygenates to liquid hydrocarbons products, including gasoline boiling range hydrocarbons and aromatics, are well known. Commercial Methanol-to-Gasoline (MTG), methanol-to olefins (MTO), Mobil Olefin to Gasoline/Distillate (MOG/D) and conversion of olefins and paraffins to aromatics (M-2 Forming) processes employ shape selective medium pore zeolite catalysts. It is understood that the present zeolite conversion unit operation can have the characteristics of these catalysts and processes to produce a variety of hydrocarbon products, especially liquid aliphatics and aromatics in the C5-C9 gasoline range. The zeolite catalyzed conversion processes can be run in fixed, fluidized or moving catalyst beds.

The various reactions which take place in the zeolite conversion reactor include oligomerization, alkylation, dehydrocyclization, isomerization and cracking. These include exothermic and endothermic reactions, which can be thermally balanced to require little or no heat exchange to maintain process reaction temperature in the fluidized bed. Mixed hydrocarbons from FCC operations, following the etherification and effluent separation, can be selected or modified to include a balance of olefins and paraffins to achieve the desired thermodynamic properties.

Description of Zeolite Catalysts

Recent developments in zeolite technology have provided a group of medium pore siliceous materials having similar pore geometry. Most prominent among these intermediate pore size zeolites is ZSM-5, which is usually synthesized with Bronsted acid active sits by incorporating a tetrahedrally coordinated metal, such as Al, Ga, Fe or mixtures thereof, within the zeolitic framework. These medium pore zeolites are favored for acid catalysis; however, the advantages of ZSM-5 structures may be utilized by employing highly siliceous materials or crystalline metallosilicate having one or more tetrahedral species having varying degrees of acidity. ZSM-5 crystalline structure is readily recognized by its X-ray diffraction pattern, which is described in U.S. Pat. No. 3,702,866 (Argauer, et al.), incorporated by reference.

Zeolite hydrocarbon upgrading catalysts preferred for use herein include the medium pore (i.e., about 5-7A) shape-selective crystalline aluminosilicate zeolites having a silica-to-alumina ratio of at least 12, a constraint index of about 1 to 12 and acid cracking activity (alpha value) of about 1–250, preferably about 3 to 80 based on total catalyst weight. In the fluidized bed reactor the coked catalyst preferably has an apparent activity (alpha value) of about 1 to 20 under the process conditions to achieve the required degree of reaction severity. Representative of the ZSM-5 type medium pore shape selective zeolites are ZSM-5, ZSM-11, ZSM-12, ZSM023, ZSM-35, and ZSM-48. Aluminosilicate ZSM-5 is disclosed in U.S. Pat. No. 3,702,886 and U.S. Pat. No. Re 29,948. Other suitable zeolites are disclosed in U.S. Pat. Nos. 3,709,979; 3,832,449; 4,076,979; 3,832,449; 4,076,842; 4,016,245; 4,414,423; 4,417,086; 4,517,396 and 4,542,251. The disclosures of these patents are incorporated herein by reference. While suitable zeolites having a coordinated metal oxide to silica molar ratio of 12:1 to 200:1 or higher may be used, it is advantageous to employ a standard ZSM-5 having a silica alumina molar ratio of about 25:1 to 70:1, suitably modified if desired to adjust acidity and oligomerization/aromatization characteristics. A typical zeolite catalyst component having Bronsted acid sits may consist essentially of aluminosilicate ZSM-5 zeolite.

Certain of the ZSM-5 type medium pore shape selective catalysts are sometimes known as pentasils. In addition to the preferred aluminosilciates, the gallosilicate, the ferrosilicate materials may be employed. ZSM-5 type pentasil zeolites are particularly useful in the process because of their regenerability, long life and stability under the extreme conditions of operation. Usually the zeolite crystals have a crystal size from about 0.01 to 2 microns or more. In order to obtain the desired particle size for fluidization in the turbulent regime, the zeolite catalyst crystals are bound with a suitable inorganic oxide, such as silica, alumina, etc. to provide a zeolite concentration of about 5 to 95 wt. %. It is advantageous to employ a standard ZSM-5 having a silica:alumina molar ratio of 25:1 or greater in a once-through fluidized bed unit to convert 60 to 100 percent, preferably at least 75 wt. %, of the monoalkenes and methanol in a single pass. In the preferred embodiment 25% H-ZSM-5 catalyst calcined with 75% silica-alumina matrix binder is employed unless otherwise stated.

Fluidized Bed Reactor Operation

Suitable olefinic feedstreams to the olefin upgrading unit comprise $C_2$–$C_4$ alkenes, including unreacted butylenes and other alkenes from the etherification operation. Non-deleterious components, such as $C_4$ lower paraffins and inert gases, may be present. The reaction severity conditions can be controlled to optimize yield of olefinic gasoline or $C_6$–$C_8$ BTX hydrocarbons, according to product demand. Reaction temperatures and contact time are also significant factors in the reaction severity, and the process parameters are followed to give a substantially steady state condition wherein the reaction severity is maintained within the limits which yield a desired wight ratio of propane to propene in the reaction effluent.

In a turbulent fluidized catalyst bed the conversion reactions are conducted in a vertical reactor column by passing hot reactant vapor or lift gas upwardly through the reaction zone at a velocity greater than dense bed transition velocity and less than transport velocity of the average catalyst particle. A continuous process is operated by withdrawing a portion of coked catalyst from the reaction zone, oxidatively regenerating the withdrawn catalyst and returning regenerated catalyst to the reaction zone at a rate to control catalyst activity and reaction severity to effect feedstock conversion. However, the processes may be operated without employing a catalyst regenerator.

In a typical process, the alkanol and olefinic feedstream is converted in a catalytic reactor under oligomerization conditions and moderate pressure (ie-100 to 2500 kPa) to produce a predominantly liquid product consisting essentially of $C_5+$ hydrocarbons rich in gasoline-range mono-olefins and aromatics. The $C_5+$ gasoline product comprises at least 45 weight percent aromatics. The use of fluidized bed catalysis allows excellent control of catalyst activity and temperature which can be used to maintain relatively constant product quality. In addition, it provides excellent flexibility to change operating conditions.

The light aliphatic hydrocarbon conversion process to form aromatics may utilize conversion conditions describe din U.S. Pat. Nos. 3,760,024 (Cattanach); 3,845,150 (Yan and Zahner); 4,097,367 (Haag et al.); 4,350,835 (Chester et al.); 4,590,323 (Chu); and 4,629,818 (Burress) incorporated herein by reference. Preferred aromatization conditions include temperatures of about 400° C.–600° C. and pressure from about 100–2000 kpa, absence of hydrogen and a weight hourly space velocity of from 0.5 to 20 WHSV. The $C_6$–$C_{10}$ aromatic products which are produced are predominantly benzene, toluene and xylene isomers (BTX) with minor amounts of other $C_6$–$C_{10}$ components.

While the instant invention has been described by specific examples and embodiments, there is no intent to limit the inventive concept except as set forth in the following claims.

What is claimed is:

1. A continuous process for the production of aromatics-rich high octane gasoline, comprising:
   - contacting a feedstream mixture containing a minor amount of lower alkanol and a major amount of light olefin comprising butene in a reaction zone containing medium pore metallosilicate catalyst under aromatization conditions at elevated temperature; and
   recovering a reaction zone effluent comprising aromatics-rich $C_5+$ gasoline.

2. The process of claim 1 wherein said feedstream mixture contains at least 80 weight percent mixed butenes.

3. The process of claim 1 wherein said feedstream mixture contains methanol in the amount of 0.1 to 5 weight percent, based on butenes.

4. The process of claim 1 comprising the further step of introducing an additional feedstream comprising $C_2$–$C_3$ lower olefins to said reaction zone.

5. The process of claim 1 wherein said aromatization conditions comprise reaction temperature of about 400° to 600° C., pressure of about 100 to 2000 kPa, and wherein said gasoline contains at least 45 wt. % $C_6$–$C_9$ aromatic hydrocarbons.

6. An improved olefin upgrading process for high octane fuel production comprising the reaction step of contacting a feedstream consisting essentially of at least one lower alkanol selected from the group consisting of methanol, ethanol, 1-propanol, isopropanol, 1-butanol and 2-butanol and light olefinic hydrocarbon rich in butenes with acidic, medium pore metallosilicate catalyst under alkanol and hydrocarbon conversion reaction conditions to produce $C_5+$ gasoline boiling range hydrocarbons containing a major amount of aromatic hydrocarbons.

7. The process of claim 6 wherein the alkanol comprises methanol and wherein the hydrocarbon consists essentially of $C_4$ paraffins and olefins.

8. The process of claim 6 wherein said alkanol consists essentially of methanol; and wherein said light olefinic hydrocarbon contains ethene or propene.

9. The process of claim 6 wherein said alkanol and hydrocarbon conversion conditions comprise reaction temperature of about 400° to 600° C., pressure of about 100 to 2000 kPa, and wherein said gasoline boiling range hydrocarbons are rich in $C_6$–$C_9$ aromatic hydrocarbons.

10. The process of claim 9 wherein said alkanol and hydrocarbon conversion reaction conditions comprise a temperature of about 425° C., pressure of about 925 kPa, and said gasoline boiling range hydrocarbons are predominantly aromatic hydrocarbons.

11. The process of claim 6 wherein said light olefinic hydrocarbons consists essentially of $C_4$ hydrocarbon containing isobutylene.

12. The process of claim 11 wherein said light hydrocarbon steam comprises about 80 weight percent mixed butanes and butenes.

13. The process of claim 6 wherein said metallosilicate catalyst comprises acid zeolite having the structure of ZSM-5; and wherein reaction conditions comprise temperature between 400° and 600° C., pressure between 100 and 2000 kPa, and said gasoline boiling range hydrocarbons are rich in distillate hydrocarbons.

14. An improved fluidized catalysis aromatization process which comprises the step of:
   contacting an olefinic hydrocarbon feedstream containing a minor amount of lower aliphatic alcohol with acidic, medium pore metallosilicate catalyst in a fluidized catalyst bed aromatization reaction zone under hydrocarbon and alcohol conversion conditions at temperature between about 400° and 600° C., pressure between about 100 and 2000 kPa whereby $C_5+$ gasoline boiling range hydrocarbons are produced comprising at least 45 weight percent aromatics.

15. The process of claim 14 wherein said alcohol comprises methanol, ethanol, 1-propanol, isopropanol, 1-butanol, 2-butanol or mixtures thereof; and wherein said metallosilicate catalyst comprises acidic, medium pore zeolite comprising ZSM-5; wherein said feedstream contains at least 80 weight percent mixed butenes; and wherein said feedstream contains alcohol in the amount of 0.1 to 5 weight percent, based on butenes.

16. The process of claim 14 comprising the further step of introducing an additional feedstream comprising $C_2$–$C_3$ lower olefins to the aromatization reaction zone.

* * * * *